United States Patent [19]

Ramachandran et al.

[11] Patent Number: 4,870,201
[45] Date of Patent: Sep. 26, 1989

[54] PROCESS FOR THE PRODUCTION OF NITRILES

[75] Inventors: Ramakrishnan Ramachandran, Allendale; Virginia A. Malik, Linden; Donald L. MacLean, Annandale; Donald P. Satchell, Jr., Summit, all of N.J.

[73] Assignee: The BOC Group, Inc., New Providence, N.J.

[21] Appl. No.: 281,581

[22] Filed: Dec. 8, 1988

[51] Int. Cl.$^4$ .................................... C07C 120/14
[52] U.S. Cl. ............................. 558/319; 558/320
[58] Field of Search ............................. 558/319, 320

[56] References Cited

U.S. PATENT DOCUMENTS

| | | | |
|---|---|---|---|
| 3,161,670 | 12/1961 | Adams et al. | 558/319 X |
| 3,176,444 | 4/1965 | Kiyonaga | 55/26 |
| 3,591,620 | 7/1971 | Yoshino et al. | 260/465.3 |
| 4,070,393 | 1/1978 | Angstadt et al. | 558/319 X |
| 4,305,886 | 12/1981 | Pujado | 558/320 X |
| 4,335,056 | 6/1982 | Callahan et al. | 260/465.3 |
| 4,498,910 | 2/1985 | Benkmann | 55/18 |
| 4,609,502 | 9/1986 | Khoobiar et al. | 260/465.3 |
| 4,754,049 | 6/1988 | Khoobiar et al. | 558/320 |

OTHER PUBLICATIONS

Gates, et al; Chemistry of Catalytic Processes, (1979), McGraw-Hill, pp. 349–350 and 380–384.
Thomas, "Catalytic Processes & Proven Catalyses," (1970), Academic Press, pp. 118–119.
Pujado, et al., "Catalylic Conversion of L.P.G.," (1986), American Institute of Chem. Eng., pp. 1–19 drawings & tables.

Primary Examiner—Joseph Paul Brust
Attorney, Agent, or Firm—Carol A. Nemetz; R. Hain Swope; Larry R. Cassett

[57] ABSTRACT

An improved process is provided for the production of nitriles from hydrocarbons by reaction with oxygen, air or a gas enriched in oxygen relative to air, preferably the latter, and ammonia in the presence of an ammoxidation catalyst. An alkane, e.g., propane, is converted to an alkene in a catalytic dehydrogenator. The product stream is introduced into an ammoxidation reactor. The product formed therein is recovered in a conventional quench tower. The gaseous effluent from the quench tower is treated in a PSA unit comprising at least two pairs of adsorptive beds. The first bed forms a gas stream containing the unreacted alkane and alkene as well as a minor amount, typically 1-2 percent by volume, of oxygen and a vent stream containing oxygen, nitrogen if present, and hydrogen. The vent stream is introduced into the second adsorptive bed to thereby form an oxygen-containing stream which also contains, nitrogen, if present, and a hydrogen-enriched stream. The oxygen-containing stream may be recycled to the ammoxidation reactor depending on the nitrogen content thereof. The alkene/alkane stream plus at least a portion of the hydrogen stream is introduced into a selective oxidation unit to remove the remaining oxygen and then recycled to the dehydrogenator. The remainer of the hydrogen-enriched stream, if any, may be taken as product or vented. The dehydrogenator may be a multistage dehydrogenator wherein the product stream is withdrawn from a reactor other than the first and last reactors, the recycle streams are introduced into the next sequential reactor and the effluent from the last reactor is introduced into the first reactor, a reactor having a similar alkane composition or directly into the admmoxidation/oxidation reactor.

18 Claims, 6 Drawing Sheets

PROCESS FOR THE PRODUCTION OF NITRILES

The present invention is directed to an improvement in ap process for producing nitriles from alkanes, an oxygen-containing gas and ammonia in the presence of a suitable catalyst under conditions which achieve high efficiency and selectivity toward the desired product.

BACKGROUND OF THE INVENTION

The production of nitriles and ammoxidation of an appropriate alkene in the presence of a suitable catalyst is well known. The production of acrylonitrile, for example, from a gaseous feed of propylene, ammonia and air is described by Bruce E. Gates et al in *Chemistry of Catalytic Processes*. McGrawHill (1979), pp. 380–384.

The feed is sent to an ammoxidation reactor where, in the presence of a suitable catalyst, acrylonitrile is produced along with lesser amounts of other nitrogen-containing compounds. The effluent from the ammoxidation reaction is quenched with water and the desired products are obtained in the liquid phase. The gas phase by-products, typically oxygen, carbon dioxide, carbon monoxide, nitrogen and unreacted hydrocarbon, are combined with natural gas and sent to a boiler for combustion as disclosed, for example, in Yoshino et al., U.S. Pat. No. 3,591,620 and Callahan et al., U.S. Pat. No. 4,335,056.

More recently, Khoobiar et al., in U.S. Pat. No. 4,609,502 disclosed a cyclic process for producing acrylonitrile using propane as a starting material which is initially dehydrogenated catalytically in the presence of steam to form propylene. This is in contrast to most conventional dehydrogenation processes and which avoid steam primarily due to the costs involved. After ammoxidation, the effluent is quenched, the desired product removed, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are by-products of dehydrogenation, and unreacted propylene in addition to carbon oxides. As an option, this gas mixture is split and a portion is sent to a separator which removes only carbon dioxide. A portion of the effluent from the separator is purged to remove light hydrocarbons. The nonpurged stream is mixed with the remainder of the oxidator effluent, fresh propane and steam, if necessary, sent to the dehydrogenator where the propane is converted to propylene. Another option is to cool and liquify the C-3 hydrocarbons therefrom and then vaporize them prior to recycle.

The aforementioned process suffers from several disadvantages. For example, there is no practical way to selectively remove by-products of propane dehydrogenation, such as methane, ethane, ethylene and the like, thereby preventing their accumulation in the system other than by removing them in the purge stream. The removal of these gases in a purge stream will result in a loss of some of the circulating propane and propylene. As the process is being carried on in a continuous manner, this loss of starting material causes a significant decrease in the yield of propylene. As mentioned above, propane and propylene can be recovered from the purge stream prior to venting. This requires additional refrigeration apparatus to cool and liquify propylene and propane. The separated C-3 hydrocarbons must be vaporized prior to recycle. These operations add to the capital costs and power requirements of the process.

Another disadvantage of the Khoobiar et al process stems from the use of the selective oxidation reactor to treat the gaseous effluent from the quencher. The gases exiting the quencher are at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three options to alleviate this problem. First, the amount of oxygen entering the oxidation reactor can be reduced by other means. Second, multiple reactors can be utilized with a cooling means between each pair of reactors. Third, a portion of the effluent from the reactor is passed through a cooling means and recycled to the feed to reduce the internal temperature of the reactor. None of these measures is attractive from the viewpoint of cost and efficiency.

The oxidation reactor in the Khoobiar et al process is operated with oxidation catalysts such as noble metals (e.g., platinum). Olefins and carbon monoxide, which are generated in the dehydrogenation reactor, are known to deactivate these catalysts, as disclosed in *Catalytic Processes and Proven Catalysts*, Charles L. Thomas, Academic Press (1970) pp. 118–119. Accordingly, multiple oxidation reactors must be used to allow for frequent regeneration of the catalyst which represents yet another addition to production costs (U.S. Pat. No. 4,609,502, column 4, lines 51–56).

It is therefore apparent that the industry is still searching for a cost effective process of converting hydrocarbons into nitriles. Applicants have discovered an improvement in processes which are cost effective and in which the disadvantages of the aforementioned systems are substantielly reduced or eliminated. Moreover, in comparison to conventional processes, the thermal requirements of the improved processes of the invention are markedly reduced.

SUMMARY OF THE INVENTION

The processes improved in accordance with the invention provide for the production of nitriles by converting a gaseous alkane to the corresponding alkene in a dehydrogenator, reacting the alkene in an ammoxidation reactor with an oxygen-containing gas, preferably oxygen-enriched air, and ammonia gas in the presence of an ammoxidation catalyst to form the desired product. The product stream is quenched with a liquid to form a liquid phase containing the desired product and a gas phase which is passed under pressure into a pressure swing adsorption (PSA) unit having an improved cycle which provides an oxygen-containing stream, a product stream containing reactant alkane and alkene hydrocarbons, a hydrogen-enriched stream and a vent stream containing carbon oxides and lower hydrocarbons. Nitrogen, in the feed stream is removed in the oxygen-containing stream. The product stream is passed into a selective oxidation unit where minor amounts of residual oxygen are removed. The effluent from the selective oxidation unit is recycled to the dehydrogenator with fresh propane feed. The oxygen-containing stream from the PSA unit may be recycled to the ammoxidation reactor, depending on the nitrogen content thereof. In one embodiment of the present invention, the PSA unit produces a hydrogen-enriched stream which may be recycled to the dehydrogenator, the selective oxidation unit or withdrawn as product. The dehydrogenator may be a single unit or a multistage unit wherein the recycle stream is admitted to a particular stage following that from which the effluent for the reactor is withdrawn. A second PSA unit may be present between the dehydrogenator and the reactor to remove hydrogen from the dehydrogenator effluent. When the second PSA unit is present, the first PSA unit does not produce a hydrogen-enriched stream.

DESCRIPTION OF THE PREFERRED EMBODIMENTS

The process of this invention is applicable to the synthesis of nitriles. In each instance, an alkene is reacted with an oxygen-containing gas comprising pure oxygen, air or a gas enriched in oxygen relative to air in the presence of a suitable catalyst. The term "suitable catalyst" indicates a catalyst that will catalyze the production of the desired product under the conditions utilized in the reactor. In the subject process the catalyst is an ammoxidation catalyst. These catalysts and their use are conventional and well known to one of ordinary skill in the art.

Illustrative of products, and their respective starting gaseous alkanes, which can be advantageously produced by the method of this invention are acrylonitrile from propane, methacrylonitrile from isobutane, ethane and the like. In the interest of brevity, the subject process will be described with reference to the production of acrylonitrile from propane, but is in no way intended to be limited thereto.

Figure 1:
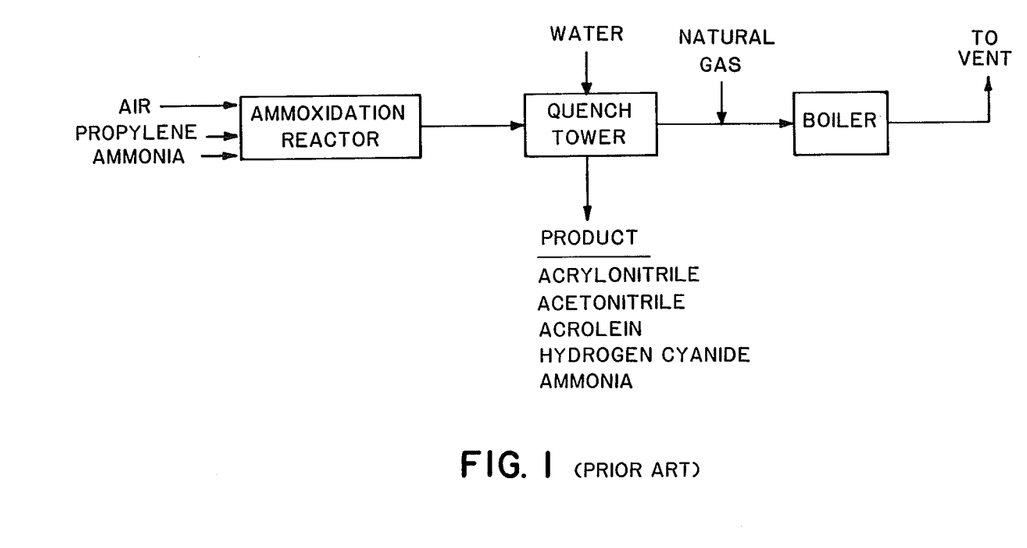
FIG. 1 illustrates in a block diagram a present conventional process of producing acrylonitrile.

Turning to the drawings, a process currently utilized commercially to produce acrylonitrile is illustrated in FIG. 1. Propylene, ammonia and air are fed into a conventional reactor containing a suitable ammoxidation catalyst. The reactor may be of any conventional fixed or fluidized bed design, typically the latter. Such processes, which do not involve a recycle step, utilize air or oxygen-enriched air in the reactor feed, although air is normally used for reasons of economy. The oxygen concentration in the reactor feed is not considered to be critical since there is no problem with accumulation of other gases, primarily nitrogen, in the system due to the lack of recycle. Those skilled in the art are aware, however, that the oxygen content in the feed of such a process must be regulated in regard to other aspects of the process.

The reactor product gases are cooled in a heat exchanger, not shown, to form steam and then passed to a water quench column or tower to dissolve the products, i.e. acrylonitrile, acetonitrile, acrolein and hydrogen cyanide, as well as unreacted ammonia. The acrylonitrile is subsequently recovered from the aqueous solution by conventional methods. The off-gases from the quench tower are combined with natural gas and combusted in a boiler to generate steam. The off-gases of the toiler are vented. Since there is no recycle provided in such a process, the yield of acrylonitrile realized is directly related to the efficiency of the reactor.

Figure 2:
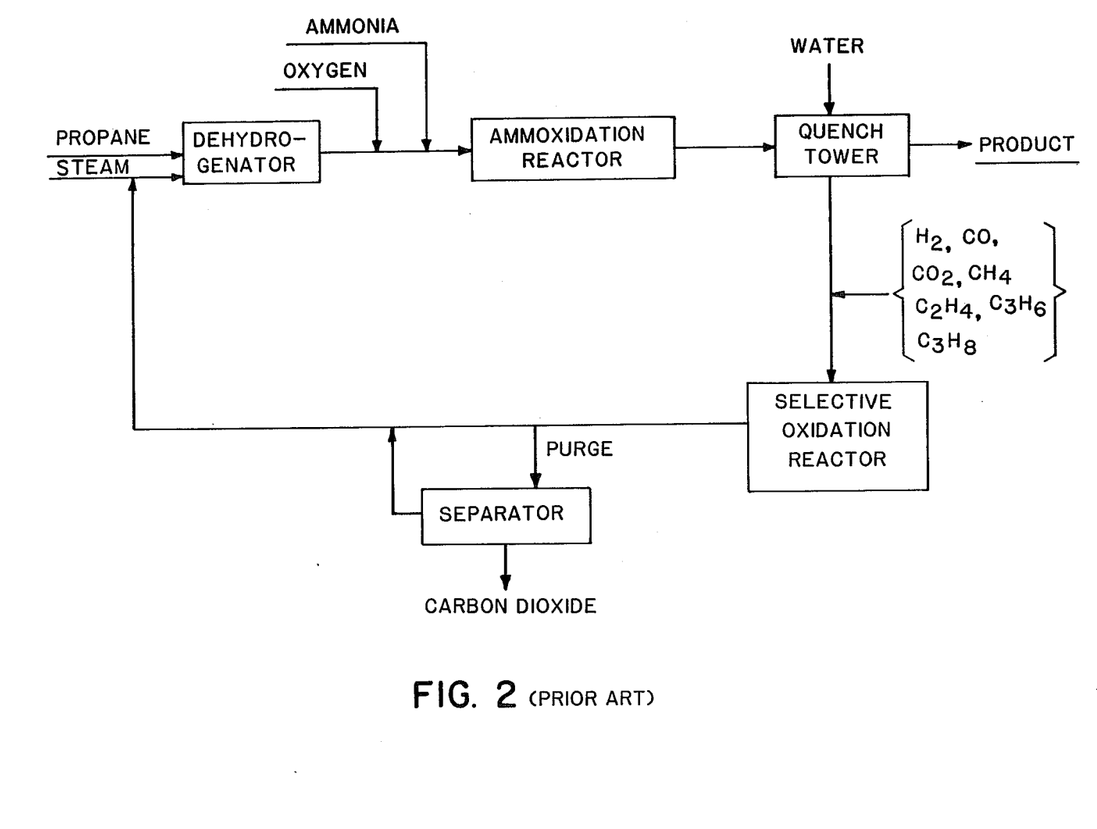
FIG. 2 illustrates in a block diagram a prior art process of producing acrylonitrile utilizing a recycle step.

FIG. 2 illustrates the cyclic process for producing acrylonitrile disclosed in Khoobiar et al U.S. Pat. No. 4,609,502. In this process, propane and steam are fed into a dehydrogenator to form propylene which is then mixed with oxygen and ammonia and fed into an ammoxidation reactor such as described in FIG. 1. The product is fed to an aqueous quench tower as in FIG. 1 and the products withdrawn in solution. The gaseous take-off from the quench tower, typically containing oxygen, hydrogen, carbon monoxide, carbon dioxide, methane, ethane, ethylene, propane and propylene, is fed to a selective oxidation reactor. As previously indicated, it is generally essential for the efficient operation of such a reactor to heat the gas mixture prior to introduction therein.

A portion of the off-gas from the oxidation reactor is passed to a separator to remove carbon oxides by an undisclosed mechanism. A portion of the separator effluent, which contains light hydrocarbons and hydrogen, is purged, treated to remove propane and propylene and discarded thereby preventing buildup of by-products in the system. The propane and propylene are combined with the remainder of the oxidator effluent and the remainder of the separator effluent and recycled to the dehydrogenator. It is, of course, necessary for the oxidator to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 3:
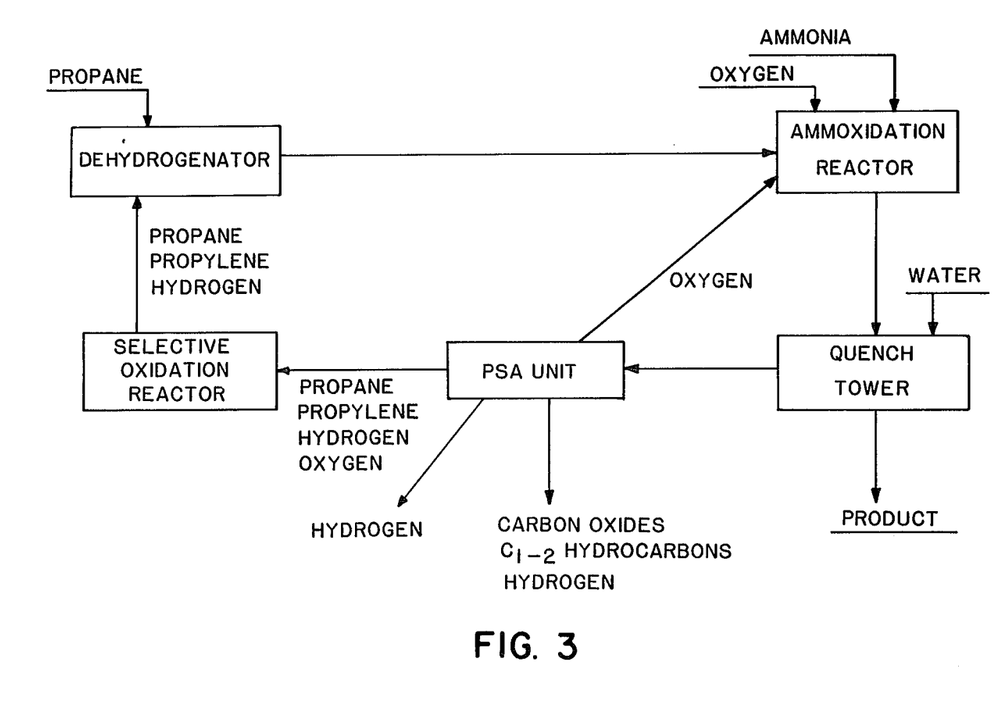
FIG. 3 illustrates in a block diagram the improvement of the invention in a process for producing acrylonitrile wherein a selective oxidation unit is downstream of the PSA unit.

The improvement in a cyclic process for producing nitriles provided in accordance with the present invention is illustrated in FIG. 3. The process shown in FIG. 3 provides the efficiency of recycle afforded by the process illustrated in FIG. 2 and is similar in a generic sense in that it contains the same kinds of functional units, yet is substantially more efficient and, unexpectedly, capable of effectively utilizing air or oxygen-enriched air as a feed to the ammoxidation reactor. Specifically, the subject process utilizes a pressure swing adsorption (PSA) unit having an operating cycle such that it will produce an oxygen-containing stream which will also contain nitrogen, in the feed stream, a product stream containing unreacted alkane/alkene hydrocarbons from the quench tower effluent, a vent stream containing carbon oxides and lower hydrocarbons and a hydrogen-enriched stream. These streams can be recycled to the ammoxidation reactor, the dehydrogenator or the selective oxidation unit, as appropriate. Since the product stream contains only a small quantity, i.e. typically 1-2 percent by volume, of oxygen, the selective oxidation reactor can be comparatively small in terms of capital expenditure and have a long life, yet still function effectively. The configuration of the subject process eliminates the substantial loss of efficiency inherent in the process of FIG. 2 by the use of the purge stream. In addition, the novel operation of the PSA unit of the subject invention provides for recycle of an oxygen-enriched stream, thus providing a further increase in process efficiency. The hydrogen-enriched stream may be recycled as well or withdrawn as product.

Referring to FIG. 3, propane is fed into the dehydrogenator where it is converted to propylene. For increased catalyst life, a hydrogen-containing gas may be introduced into the dehydrogenator with the propane feed. The required amount of hydrogen can conveniently be provided through the recycle stream from the PSA unit as will be discussed below. The hydrogen-containing gas can, if desired, be provided as a discrete stream. The dehydrogenator can be of any design including a multistage dehydrogenator, as will be discussed hereafter. The catalyst utilized in the dehydrogenator can be any conventional dehydrogenation catalyst, preferably one or more Group VIII noble metals such as platinum on an alumina support. A steam-assisted dehydrogenator may be utilized as well.

The effluent product stream from the dehydrogenator, comprising unreacted propane, propylene and hydrogen, is fed into a conventional ammoxidation reactor along with pure oxygen, air or, preferably oxygen-enriched air and ammonia. The system shown in FIGS. 3 and 4 utilizes pure oxygen as a feed. In the event that an oxygen-enriched stream is recycled from the PSA unit, it may be introduced independently or in combination with the oxygen feed. The relative proportions of each can be adjusted to achieve the desired amount of oxygen in the reactor. In the event that the feed to the ammoxidation reactor is air or oxygen-enriched air, the oxygen-containing stream produced by the PSA unit may be vented or only partially recycled to the reactor. The amount of the oxygen-containing stream produced by the PSA unit which is vented will depend on the oxygen content of the reactor feed and the desired reactor pressure. The venting of the oxygen-containing stream through a purge line, not shown, thereby prevents the accumulation of nitrogen in the system. These considerations apply as well to the system shown in FIGS. 5 and 6 which is also illustrated with a pure oxygen feed.

The ammoxidation reactor utilized in the present process is conventional and may employ either a fixed or fluidized catalyst bed. A typical example of an ammoxidation reactor is disclosed in Angstadt et al., U.S. Pat. No. 4,070,393 and Gates et al., ibid, pp. 381–383, each incorporated herein by reference. The reactor contains a conventional ammoxidation catalyst, such as bismuth-molybdenum oxide, iron-antimony oxide, uranium-antimony oxide precipitated on silica and the like. Other suitable catalysts are disclosed, for example, in *Chemistry of Catalytic Processes*. Gates et al, McGraw Hill (1979) pp. 349–350, and Yoshino et al, U.S. Pat. No. 3,591,620, incorporated herein by reference. Additional suitable catalysts are known to those skilled in the art.

The ammoxidation reaction is conducted at a temperature of from about 375° to 550° C., preferably from about 400° to 500° C., at low pressures, typically in the range of from about 3 to 30 psig, preferably from about 5 to 20 psig. The reactants are passed through the reactor at a relatively low velocity, typically in the range of from about 1.75 to 2.2 ft./sec. The oxygen-containing gas feed may be pure oxygen, air or oxygen-enriched air. In accordance with this invention, oxygen-enriched air preferably contains from about 30 to about 80, most preferably from about 55 to 65, percent by volume of oxygen. Such mixtures may be produced by adjusting the capacity of a conventional oxygen-producing unit, e.g. a conventional PSA unit, or by mixing pure oxygen with air in the proper proportions. The ratio of oxygen to propylene in the feed is suitably in the range of from about 1.6:1 to 2.4:1 by volume. The ratio of ammonia to propylene in the feed is suitably in the range of from about 0.7 to 1.2:1 by volume.

The effluent from the ammoxidation reactor comprises a major amount of acrylonitrile and minor amounts of acrolein, hydrogen cyanide, acetonitrile, carbon oxides and nitrogen, when present in the feed, as well as unreacted oxygen, propylene and propane. This gaseous mixture is quenched or scrubbed with a liquid, such as water, to dissolve the water-soluble compounds for subsequent separation and recovery of acrylonitrile, acetonitrile and hydrogen cyanide. The quench liquid may be made slightly acidic with suitable acid such as sulfuric acid, to aid in the removal of ammonia as is known in the art.

The gas phase effluent from the quench step is introducing into a PSA unit. PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and description or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudo continuous flow of desired product. It is preferred to pass the quench tower effluent through a conventional dryer (not shown) to remove moisture therefrom prior to introducing it into the PSA unit.

It may be necessary to raise the pressure of the quench tower effluent in a compressor or other suitable means prior to introducing it into the PSA unit. The compressor increases the pressure of the quench tower gaseous effluent to the operating pressure of a PSA unit, typically from about 3 to 50 psig, preferably from about 20 to 40 psig. These ranges may vary to an extent depending on the adsorbent in the PSA unit. It may also be necessary to pass the effluent through a conventional dryer, not shown, prior to introduction into the PSA unit.

The PSA system utilized in accordance with the present invention comprises at least two pairs of adsorptive beds functioning in series. The quench tower effluent entering the PSA unit consists of light hydrocarbons, i.e. propane, propylene ethane, ethylene and methane, carbon monoxide, carbon dioxide, hydrogen, oxygen and nitrogen. The adsorbent in the first bed can be any art-recognized material which will adsorb C-3 hydrocarbons preferentially to the other gases. Silica gel and activated carbon are preferred adsorbent materials. Silica gel is a particularly preferred material wherein oxygen-enriched air is utilized as a reactor feed material. An unadsorbed stream containing hydrogen, oxygen and nitrogen, flowing through the first bed is introduced into the second bed. The PSA unit is operated such that the nonadsorbed stream flowing through the first bed is not flammable. In the next step of the PSA cycle, the pressure in the bed is lowered to a value such that a vent stream, which contains the remaining light hydrocarbons, can be withdrawn from the outlet of the bed with minima desorption of product hydrocarbons. The vent stream may be either vented or incinerated. The hydrocarbon product recycle stream is then produced conventionally at the inlet by desorbing the bed.

The adsorbent in the second bed of the PSA unit is selected so that it will adsorb oxygen, and nitrogen in preference to hydrogen, e.g. a molecular sieve zeolite. The second bed is operated in such a manner that the oxygen in the nonadsorbed effluent flowing therethrough is below flammability levels. The second bed produces a recycle stream of predominately oxygen and nitrogen and a stream rich in hydrogen. The latter stream may be vented, taken as product or recycled to the dehydrogenator to maintain a desired level of hydrogen therein. The PSA unit is operated in a manner such that none of the streams produced thereby is flammable and the concentration of oxygen and hydrogen in their respective streams is maximized. For example, flammability of the oxygen-containing stream is suppressed by withdrawing it fuel-rich, i.e. containing a high percentage of hydrogen and light hydrocarbons.

Since the hydrogen-rich stream produced in the PSA unit may contain some oxygen, it is not introduced directly into the dehydrogenator, but is instead introduced into the selective oxidation reactor with the hydrocarbon recycle stream. The amount of hydrogen required in the recycle feed to the dehydrogenator or the selective oxidator will vary with the catalyst and can be determined by operation of the system utilizing a given catalyst.

In the event that the feed to the ammoxidation reactor is pure oxygen, the PSA unit produces an oxygen-enriched stream of product quality which is recycled to the reactor. As the percentage of nitrogen in the reactor feed increases, however, the amount of the oxygen stream that is recycled decreases to prevent the accumulation of nitrogen in the system. Even in the event that the oxygen-containing stream produced in the PSA unit is totally purged, the process of the invention is advantageous in that oxygen loss is minimal and nitrogen build-up is prevented without the loss of an appreciable amount of reactant hydrocarbons.

While it is preferred that the two adsorbent beds in the PSA unit be contained in separate vessels, it is within the scope of the present invention to utilize two discrete layers of adsorbent in a single vessel configured to provide the streams as described herein. In such a two-layered vessel, for example, the vent stream containing light hydrocarbons and carbon oxides would be withdrawn from an intermediate level of the vessel without passing through the second layer.

The PSA product stream withdrawn from the first bed of the PSA unit and introduced into the selective oxidation reactor contains propane, propylene, a minor quantity of oxygen, typically about 1-2 percent by volume, and nitrogen, if present in the feed. The selective oxidation reactor is of conventional configuration and contains an art-recognized catalyst capable of selectively catalyzing the reaction of oxygen and hydrogen to form water, i.e. the oxidation of hydrogen, without causing oxidation of the desired hydrocarbons, i.e. propane and propylene in the PSA effluent. Such catalysts and their use are well known. Suitable catalysts include noble metals or base metals, particularly platinum or palladinm on alumina.

As previously stated, the selective oxidation reactor utilized in the embodiment of the present process shown in FIG. 3 requires only a modest capital expenditure in comparison with the multiple bed unit contemplated in the process illustrated in FIG. 2 since the PSA effluent in the subject process contains about 1-2 percent by volume of oxygen. Typically, the oxygen content of the PSA effluent in the present process is on the order of from about 0.01 to 1 percent by volume. Since the oxygen content is at such a low level, a small oxidation reactor consisting of a single bed without the need for catalyst regeneration over a period of several years is more than adequate in the method of this invention.

The effluent from the selective oxidation reactor, predominately propane and propylene, is recycled to the dehydrogenator. In the embodiment shown in FIG. 3, this recycle stream is combined with fresh feed and admitted to the dehydrogenator. In an alternative embodiment of the subject invention, the recycle stream is introduced into the latter stage of a multistage dehydrogenator as will be discussed hereafter.

The oxygen-containing stream produced by the PSA unit of this invention generally contains from about 70 to about 95 percent of the unreacted oxygen in the quench tower effluent, depending on the amount of nitrogen present. The fact that the process of this invention provides an oxygen-containing stream is advantageous for two reasons. First, the PSA unit effectively removes all but less than about one percent of the oxygen present in the quench tower effluent stream. Therefore, little is required to remove the rest as described above. Second, by returning such a high percentage of unreacted oxygen to the ammoxidation reactor, the PSA process of this invention significantly increases the overall efficiency of the process when the feed to the reactor contains a high percentage of oxygen. These benefits are realized by all embodiments of the present invention.

Figure 4:
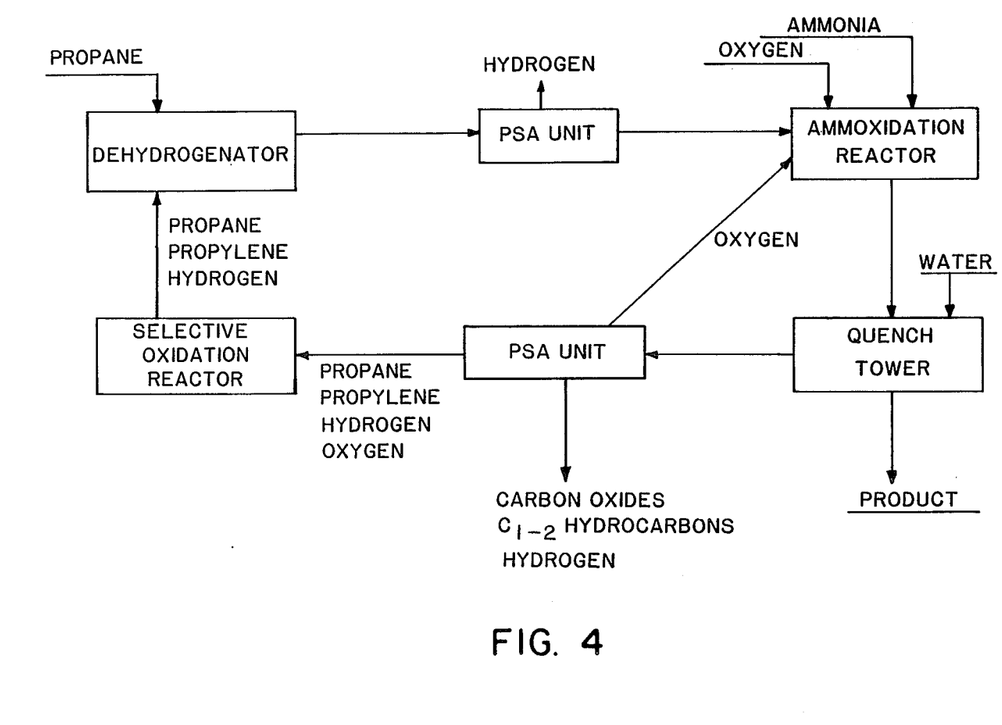
FIG. 4 illustrates in a block diagram the process of FIG. 3 wherein an additional PSA unit removes hydrogen from the dehydrogenator effluent.

In the embodiment of the present invention illustrated in FIG. 4, a second PSA unit is added to the process shown in FIG. 3. This second PSA unit is located between the dehydrogenator and the ammoxidation reactor. Although the process shown in FIG. 4 is a modification of that shown in FIG. 3, a second PSA unit may likewise be added to the system illustrated in FIG. 5 to function in a like manner. The second PSA unit present in the process illustrated in FIG. 4 contains as adsorbent, such as silica gel or activated carbon, which will strongly adsorb C-3 hydrocarbons and permit hydrogen to pass through. The resulting hydrogen-enriched stream may be vented or partially recycled as described herein, i.e., to the selective oxidation reactor or the dehydrogenator. When the optional second PSA unit is present in the system, the novel PSA unit of the present invention will not produce a hydrogen-enriched stream.

Figure 5:
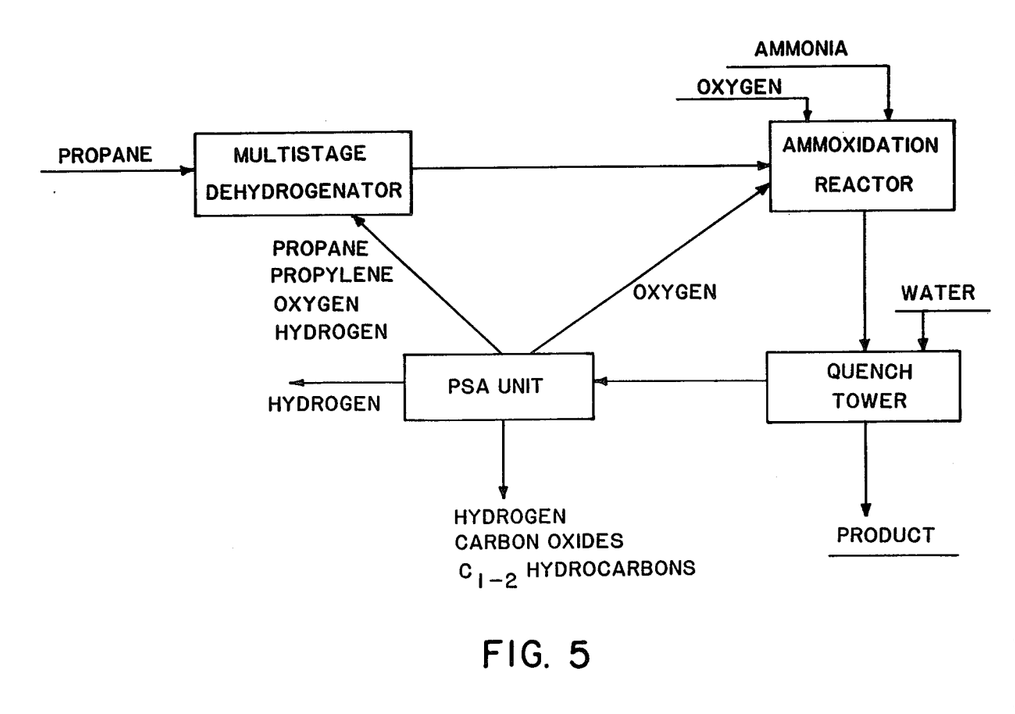
FIG. 5 illustrates in a block diagram the improvement of the invention in a process for producing acrylonitrile utilizing a multistage dehydrogenator without a selective oxidation unit downstream of the PSA unit.

Turning to FIG. 5, the dehydrogenator utilized is a multistage unit which eliminates the need for the selective oxidation reactor. The use of a multistage catalytic reactor is described in the literature, e.g. pujado et al in a paper entitled "Catalytic Conversion of LpG" presented at the American Institute of Chemical Engineers, Apr. 6-10, 1986. In such reactors, the catalyst sequentially flows through a series of discrete reactors and is withdrawn at the end for regeneration and recycle. The reactant gas stream likewise flows through the reactors and is withdrawn into a heating means between each of the individual reactors. The dehydrogenator typically operates at a temperature of from about 500° to 800° C., preferably from about 600° to 700° C. The reheating of the reactant stream as it flows through the reactors is especially beneficial for an endothermic reaction such as the conversion of propane to propylene.

In the multistage dehydrogenator shown in FIG. 5, the reactant gas stream does not flow through all of the reactors, but is withdrawn as a product stream intermediate the first and last reactors. preferably, there are at least four reactors and the product stream is withdrawn from the penultimate reactor. It is beneficial to withdraw the product stream from a latter stage of the dehydrogenator to obtain maximum efficiency therefrom. The reheating of the reactor stream takes place only up to and including the reactor from which the product stream is withdrawn.

The recycle product stream from the PSA unit of the present invention, which is comprised of unreacted alkane and alkene and a minor amount of oxygen, is introduced into the reactor following that from which the product stream is withdrawn, passed therethrough and through subsequent reactors, if any. The low oxygen content thereof can be eliminated without detriment to the system. Therefore, the selective oxidator present in the embodiments of the present invention shown in FIGS. 3 and 4 can be eliminated. The hydrogen-enriched stream produced in the PSA unit may be introduced into the dehydrogenator, taken as product, or vented. The detail of the multistage dehydrogenator utilized in accordance with the present invention is shown in FIG. 6.

Figure 6:
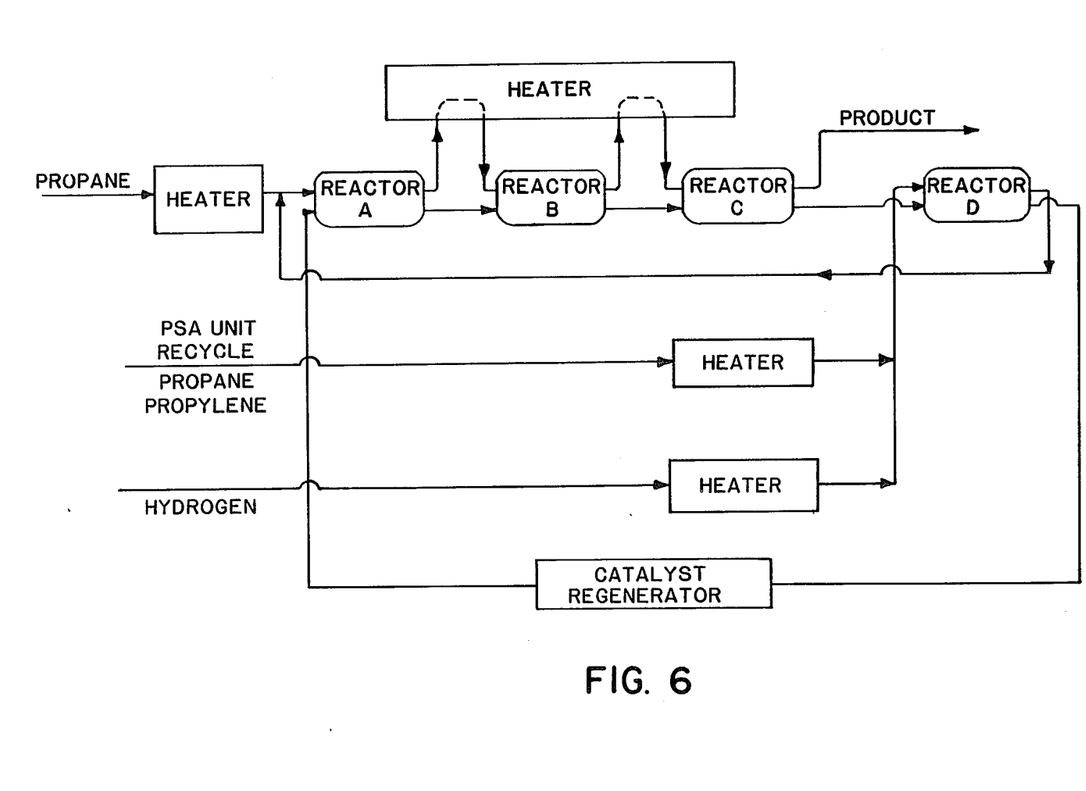
FIG. 6 illustrates in a block diagram detail of the multistage dehydrogenator shown in FIG. 5.

In the embodiment shown in FIG. 6, the effluent from the final reactor of the dehydrogenator is introduced into the initial feed stream. In the event that the feed to one of the intermediate reactors more closely approximates the effluent in regard to the concentration of the alkene than the initial feed, the effluent is introduced into such intermediate reactor. It is further contemplated to introduce the effluent from the final reactor directly into the ammoxidation reactor if the alkene content thereof is sufficiently high. This might occur, for example, when the PSA effluent passes through two or more reactors of the dehydrogenator.

The hydrocarbon recycle stream from the PSA unit of this invention contains practically no hydrogen. Therefore, a portion of the hydrogen stream produced by the PSA unit may be combined with the hydrocarbon recycle stream and reintroduced into the multistage dehydrogenerator. A portion of the hydrogen stream can likewise be introduced into the initial feed to the multistage dehydrogenator to prolong the life of the catalyst therein.

It is contemplated herein, although not necessary, to add a second PSA unit on the effluent from the dehydrogenator to remove hydrogen therefrom. The hydrogen thus obtained may be vented, recycled to the dehydrogenator feed or supplied to the heater in combination with an oxygen feed for combustion. As in the embodiment shown in FIG. 4, the first PSA unit will not produce a hydrogen-enriched stream when the second PSA unit is present. It will be appreciated by those skilled in the art that a single heater can be utilized in FIG. 6 with all streams flowing therethrough.

Utilizing a system as shown in FIG. 3 for the production of acrylonitrile utilizing propane as the starting material, the flow rates at various points in the system were determined and are presented in Table I. The flow rates are expressed in mole percent based on 100 moles of acrylonitrile produced. The propane feed was virtually 100 percent propane. The fresh feed added to the dehydrogenator effluent prior to introduction into the ammoxidation reactor was 32.88 percent of ammonia and 67.12 percent of pure oxygen. The data expressed in Table I represents operation of the system under conditions such that 80 percent and 97 percent, respectively, of the propylene in the feed to the ammoxidation reactor is converted to different products, including acrylonitrile, in the ammoxidation reactor.

In Table I, Point A is the feed into the dehydrogenator after the stream from the selective oxidation reactor has been combined with fresh propane, Point B is the combined feed into the ammoxidation reactor, Point C is the ammoxidation reactor effluent, Point D is the quench tower gaseous effluent to the PSA unit, Point E is the hydrocarbon-rich recycle stream from the PSA unit and Point F is the oxygen-enriched recycle from the PSA unit. As previously mentioned, the amount of hydrogen in the feed to the dehydrogenator will vary with the catalyst and reaction conditions used, and may be negligible. For purposes of the comparative results given in Tables I, II and III, the hydrogen to propane ratio in the dehydrogenator feed, Point A was kept at about 0.5.

TABLE I

| Component | A | B | C | D | E | F |
|---|---|---|---|---|---|---|
| 80 Percent Conversion - Pure Oxygen Feed | | | | | | |
| Propylene | 0.7 | 10.0 | 0.3 | 0.5 | 1.7 | — |
| Propane | 61.6 | 14.1 | 13.4 | 21.5 | 79.2 | 0.9 |
| Oxygen | — | 20.2 | 4.0 | 8.0 | 3.2 | 9.3 |
| CO | 0.2 | 0.4 | 1.1 | 1.2 | 0.5 | 1.4 |
| $CO_2$ | 4.0 | 1.7 | 3.7 | 3.3 | 9.2 | 0.7 |
| Acrylonitrile | — | — | 6.5 | — | — | — |
| Acrolein | — | — | 0.1 | — | — | — |
| Acetonitrile | — | — | 0.1 | — | — | — |
| HCN | — | — | 1.5 | — | — | — |
| Water | 2.8 | 1.1 | 27.4 | — | — | — |
| Ammonia | — | 9.5 | 1.0 | — | — | — |
| Methane | 0.2 | 0.8 | 0.8 | 1.3 | 0.5 | 1.5 |
| Ethane | 0.3 | 1.0 | 1.0 | 1.6 | 0.6 | 1.8 |
| Ethylene | 0.1 | 0.2 | 0.2 | 0.3 | 0.1 | 0.4 |
| Hydrogen | 30.2 | 40.9 | 39.0 | 62.4 | 5.0 | 84.1 |
| 97 Percent Conversion - Pure Oxygen Feed | | | | | | |
| Propylene | 0.6 | 8.7 | 0.2 | 0.4 | 1.4 | — |
| Propane | 60.2 | 14.0 | 13.1 | 21.1 | 75.1 | 0.9 |
| Oxygen | — | 21.4 | 4.0 | 8.1 | 3.1 | 9.5 |
| CO | 0.2 | 0.4 | 1.2 | 1.2 | 0.5 | 1.4 |
| $CO_2$ | 6.2 | 2.7 | 5.7 | 5.2 | 14.1 | 1.1 |
| Acrylonitrile | — | — | 6.0 | — | — | — |
| Acrolein | — | — | 0.1 | — | — | — |
| Acetonitrile | — | — | 0.1 | — | — | — |
| HCN | — | — | 1.3 | — | — | — |
| Water | 2.8 | 1.1 | 27.5 | — | — | — |
| Ammonia | — | 9.0 | 1.0 | — | — | — |
| Methane | 0.2 | 0.8 | 0.8 | 1.2 | 0.5 | 1.4 |
| Ethane | 0.3 | 1.0 | 1.0 | 1.5 | 0.6 | 1.8 |
| Ethylene | 0.1 | 0.2 | 0.2 | 0.3 | 0.1 | 0.4 |
| Hydrogen | 29.5 | 40.0 | 37.9 | 61.0 | 4.7 | 83.4 |

Aging utilizing system as shown in FIG. 3 for the production of acrylonitrile with propane as a starting material, the oxygen feed to the ammoxidation reactor was changed to an equal mixture of pure oxygen and air which produced oxygen-enriched air containing approximately 60 percent by volume to oxygen. The flow rates at various points in the system were determined and are presented in Table II. The data expressed in Table II represents operation of the system under conditions such that 80 percent and 97 percent, respectively, of the propylene in the feed to the ammoxidation reactor is converted therein to different products, including acrylonitrile.

TABLE II

| Component | A | B | C | D | E | F |
|---|---|---|---|---|---|---|
| 80 Percent Conversion - Equal Parts Pure Oxygen and Air | | | | | | |
| Propylene | 0.7 | 8.9 | 0.3 | 0.4 | 1.5 | — |
| Propane | 58.7 | 12.6 | 12.1 | 18.3 | 70.8 | 0.8 |
| Oxygen | — | 18.5 | 4.0 | 7.5 | 3.2 | 8.7 |
| CO | 0.2 | 0.3 | 0.9 | 1.0 | 0.4 | 1.1 |
| $CO_2$ | 3.8 | 1.5 | 3.3 | 2.8 | 8.3 | 0.6 |
| Acrylonitrile | — | — | 5.9 | — | — | — |
| Acrolein | — | — | 0.1 | — | — | — |
| Acetonitrile | — | — | 0.1 | — | — | — |
| HCN | — | — | 1.3 | — | — | — |
| Water | 2.9 | 1.0 | 24.6 | — | — | — |
| Ammonia | — | 8.7 | 1.0 | — | — | — |
| Methane | 0.2 | 0.6 | 0.6 | 0.8 | 0.4 | 1.0 |
| Ethane | 0.2 | 0.7 | 0.7 | 1.1 | 0.4 | 1.2 |
| Ethylene | — | 0.2 | 0.1 | 0.2 | 0.1 | 0.2 |
| Hydrogen | 28.0 | 28.1 | 26.9 | 40.6 | 3.4 | 54.6 |
| Nitrogen | 5.3 | 18.9 | 18.2 | 27.4 | 11.5 | 31.7 |
| 97 Percent Conversion - Equal Parts Pure Oxygen and Air | | | | | | |
| Propylene | 0.6 | 8.7 | 0.2 | 0.4 | 1.4 | — |
| Propane | 57.3 | 12.4 | 11.7 | 17.6 | 67.0 | 0.8 |
| Oxygen | — | 19.4 | 4.0 | 7.5 | 3.1 | 8.8 |
| CO | 0.2 | 0.3 | 1.0 | 1.0 | 0.4 | 1.2 |
| $CO_2$ | 5.9 | 2.3 | 5.1 | 4.3 | 12.5 | 1.0 |
| Acrylonitrile | — | — | 5.3 | — | — | — |
| Acrolein | — | — | 0.1 | — | — | — |
| Acetonitrile | — | — | 0.1 | — | — | — |
| HCN | — | — | 1.2 | — | — | — |
| Water | 2.9 | 1.1 | 24.4 | — | — | — |
| Ammonia | — | 8.0 | 1.0 | — | — | — |
| Methane | 0.2 | 0.6 | 0.5 | 0.8 | 0.3 | 0.9 |
| Ethane | 0.2 | 0.7 | 0.7 | 1.0 | 0.4 | 1.2 |
| Ethylene | — | 0.1 | 0.1 | 0.1 | 0.1 | 0.2 |
| Hydrogen | 27.2 | 27.5 | 25.9 | 39.0 | 3.2 | 53.0 |
| Nitrogen | 5.5 | 19.9 | 18.8 | 28.2 | 11.7 | 33.0 |

Utilizing a system as shown in FIG. 4 for the production of acrylonitrile using propane as the starting material, the flow rates at various points in the system are presented in Table III. The propane, ammonia and pure oxygen feeds were as in Table I. The system was operated to convert 80 and 97 percent, respectively, of the propylene feed to the ammoxidation reactor to products.

In Table III, Point A is the feed into the dehydrogenator after the recycle stream has been combined therewith, Point B is the dehydrogenerator effluent, Point C is the total feed into the ammoxidation reactor, Point D is the ammoxidation reactor effluent, Point E is the quench tower gaseous effluent, and Point F is the hydrocarbon rich recycle system to the selective oxidation reactor and Point G is the oxygen-containing gas recycle from the PSA unit.

TABLE III

| Component | A | B | C | D | E | F | G |
|---|---|---|---|---|---|---|---|
| 80 Percent Conversion - Pure Oxygen Feed | | | | | | | |
| Propylene | 0.7 | 18.7 | 11.2 | 0.3 | 0.5 | 1.7 | — |
| Propane | 60.6 | 30.2 | 15.7 | 14.7 | 25.3 | 78.5 | 1.2 |
| Oxygen | 1.2 | — | 22.3 | 4.0 | 8.6 | 2.9 | 10.8 |
| CO | 0.2 | 0.2 | 0.7 | 1.5 | 1.4 | 0.5 | 1.7 |
| $CO_2$ | 2.9 | 3.2 | 2.0 | 4.2 | 3.9 | 9.2 | 0.9 |
| Acrylonitrile | — | — | — | 7.2 | — | — | — |
| Acrolein | — | — | — | 0.1 | — | — | — |
| Acetonitrile | — | — | — | 0.1 | — | — | — |
| HCN | — | — | — | 1.6 | — | — | — |
| Water | — | — | — | 30.6 | — | — | — |
| Ammonia | — | — | 10.6 | 1.0 | — | — | — |
| Methane | 0.7 | 1.4 | 2.9 | 2.7 | 4.7 | 1.6 | 5.9 |
| Ethane | 0.8 | 1.7 | 3.7 | 3.4 | 5.9 | 2.0 | 7.4 |
| Ethylene | 0.2 | 0.3 | 0.7 | 0.7 | 1.2 | 0.4 | 1.5 |
| Hydrogen | 31.7 | 44.4 | 30.1 | 28.0 | 48.4 | 3.3 | 70.6 |

TABLE III-continued

| Component | A | B | C | D | E | F | G |
|---|---|---|---|---|---|---|---|
| 97 Percent Conversion - Pure Oxygen Feed | | | | | | | |
| Propylene | 0.6 | 18.3 | 9.7 | 0.3 | 0.5 | 1.4 | — |
| Propane | 59.2 | 29.6 | 15.6 | 14.2 | 24.7 | 74.4 | 1.2 |
| Oxygen | 1.2 | — | 23.6 | 4.0 | 8.7 | 2.9 | 11.1 |
| CO | 0.2 | 0.2 | 0.8 | 1.5 | 1.4 | 0.5 | 1.8 |
| $CO_2$ | 6.1 | 5.1 | 3.2 | 6.5 | 6.1 | 14.1 | 1.5 |
| Acrylonitrile | — | — | — | 6.6 | — | — | — |
| Acrolein | — | — | — | 0.1 | — | — | — |
| Acetonitrile | — | — | — | 0.1 | — | — | — |
| HCN | — | — | — | 1.4 | — | — | — |
| Water | — | — | — | 30.6 | — | — | — |
| Ammonia | — | — | 9.9 | 1.0 | — | — | — |
| Methane | 0.7 | 1.3 | 2.9 | 2.6 | 4.6 | 1.5 | 5.8 |
| Ethane | 0.8 | 1.7 | 3.6 | 3.3 | 5.7 | 1.9 | 7.3 |
| Ethylene | 0.2 | 0.3 | 0.7 | 0.7 | 1.2 | 0.4 | 1.5 |
| Hydrogen | 31.0 | 43.5 | 29.9 | 27.2 | 47.2 | 3.1 | 69.9 |

TABLE IV

| Component | A | B | C | D | E | F | G |
|---|---|---|---|---|---|---|---|
| 80 Percent Conversion - Equal Parts Pure Oxygen and Air | | | | | | | |
| Propylene | 0.7 | 17.5 | 9.1 | 0.3 | 0.4 | 1.4 | — |
| Propane | 55.8 | 28.2 | 12.8 | 12.1 | 18.4 | 65.1 | 0.8 |
| Oxygen | 1.4 | — | 18.8 | 4.0 | 7.6 | 2.9 | 9.3 |
| CO | 0.2 | 0.2 | 0.5 | 1.1 | 1.0 | 0.4 | 1.2 |
| $CO_2$ | 3.6 | 3.0 | 1.6 | 3.4 | 2.9 | 7.7 | 0.7 |
| Acrylonitrile | — | — | — | 5.9 | — | — | — |
| Acrolein | — | — | — | 0.1 | — | — | — |
| Acetonitrile | — | — | — | 0.1 | — | — | — |
| HCN | — | — | — | 1.3 | — | — | — |
| Water | — | — | — | 25.1 | — | — | — |
| Ammonia | — | — | 8.8 | 1.0 | — | — | — |
| Methane | 0.4 | 1.0 | 1.2 | 1.1 | 1.7 | 0.7 | 2.1 |
| Ethane | 0.4 | 1.3 | 1.5 | 1.4 | 2.1 | 0.8 | 2.6 |
| Ethylene | 0.1 | 0.3 | 0.3 | 0.3 | 0.4 | 0.2 | 0.5 |
| Hydrogen | 28.4 | 40.9 | 9.9 | 9.3 | 14.2 | 1.1 | 20.2 |
| Nitrogen | 9.2 | 7.8 | 35.6 | 33.6 | 51.3 | 19.7 | 62.6 |
| 97 Percent Conversion - Equal Parts Pure Oxygen and Air | | | | | | | |
| Propylene | 0.6 | 17.0 | 7.7 | 0.2 | 0.3 | 1.2 | — |
| Propane | 54.2 | 27.6 | 12.4 | 11.5 | 17.4 | 61.4 | 0.8 |
| Oxygen | 1.4 | — | 19.5 | 4.0 | 7.6 | 2.9 | 9.3 |
| CO | 0.2 | 0.2 | 0.5 | 1.1 | 1.0 | 0.4 | 1.2 |
| $CO_2$ | 5.6 | 4.7 | 2.5 | 5.2 | 4.3 | 11.6 | 1.0 |
| Acrylonitrile | — | — | — | 5.3 | — | — | — |
| Acrolein | — | — | — | 0.1 | — | — | — |
| Acetonitrile | — | — | — | 0.1 | — | — | — |
| HCN | — | — | — | 1.1 | — | — | — |
| Water | — | — | — | 24.6 | — | — | — |
| Ammonia | — | — | 8.1 | 1.0 | — | — | — |
| Methane | 0.3 | 1.0 | 1.1 | 1.1 | 1.6 | 0.6 | 2.0 |
| Ethane | 0.4 | 1.2 | 1.4 | 1.3 | 2.0 | 0.8 | 2.5 |
| Ethylene | 0.1 | 0.3 | 0.3 | 0.3 | 0.4 | 0.2 | 0.5 |
| Hydrogen | 27.6 | 39.9 | 9.6 | 8.9 | 13.4 | 1.0 | 19.1 |
| Nitrogen | 9.7 | 8.2 | 37.0 | 34.4 | 52.0 | 20.0 | 63.7 |

The system shown in FIG. 4 was utilized for the production of acrylonitrile with propane as the starting material and utilizing an equal mixture of pure oxygen and air is shown in Table II. The results are reputed in Table IV, again operating the system to produce 80 and 97 percent conversion, respectively, of the propylene in the feed to products.

The process of this invention is advantageous in that it is very efficient and is cost attractive in comparison to prior art processes. It is readily apparent from the data presented in Tables I, II and III that, in contrast to the subject process, the process illustrated in FIG. 2 continually removes propane and propylene from the system, thereby sharply reducing the efficiency thereof. It is stated in the Khoobiar et al patent that propane and propylene are removed from the purge stream before it is vented. This would require an additional sizable capital expenditure for the refrigeration equipment required for the recovery procedure as well as an on-going cost in power to operate the recovery unit. The process of the invention has a comparatively small incidence of build-up of any of the components of the various gaseous streams formed or separated at any stage thereof. Further, the subject process can be utilized with air or an oxygen-enriched air feed, heretofore not feasible with a closed loop system. Unexpectedly, the subject process operates at particularly enhanced efficiency with an oxygen-enriched air feed.

The invention has been described with reference to preferred embodiments thereof. It will be appreciated by those skilled in the art that various modifications may be made from the specific details given without departing from the spirit and scope of the invention.

We claim:

1. In a process for the production of alpha, beta olefinically unsaturated nitriles comprising:
   (a) forming an alkene from a gaseous alkane in a catalytic dehydrogenator;
   (b) introducing a gaseous stream comprising said alkene, pure oxygen, air or a gas-enriched in oxygen relative to air and ammonia into a suitable reactor and reacting them in the vapor phase in the presence of an ammoxidation catalyst to produce a gaseous effluent containing said nitrile;
   (c) quenching said effluent in a liquid to form a liquid phase containing said nitrile and a gaseous phase;
   (d) recovering said nitrile from said liquid phase;
   (e) introducing the gaseous phase under pressure into a pressure swing adsorption unit to thereby form a gaseous stream comprising said unreacted alkane and alkene, a minor amount of oxygen and nitrogen when air or oxygen-enriched air is introduced into the reactor in step (b);
   (f) introducing said gaseous stream into a catalytic selective oxidation unit to remove the remaining oxygen in said stream; and
   (g) recycling the effluent from the selective oxidation unit to the dehydrogenator, the improvement wherein pressure swing adsorption unit comprises at least two pairs of adsorptive beds, in series, wherein the first of said pairs of beds preferentially adsorbs said alkane and alkene to other gases, thereby forming a gaseous stream containing them and a vent stream comprising oxygen, hydrogen and nitrogen, when present, which is introduced into the second of said pairs of beds, thereby forming a stream containing oxygen and nitrogen, when present, and hydrogen-enriched stream.

2. A process in accordance with claim 1, wherein the recycled effluent from the selective oxidation unit is combined with fresh alkane feed before introduction into dehydrogenator.

3. A process in accordance with claim 1, wherein the alkane is propane, the alkene is propylene and the nitrile produced is acrylonitrile.

4. A process in accordance with claim 1, wherein oxygen is added in step (b) as oxygen-enriched air containing from about 30 to about 80 percent of oxygen by volume.

5. A process in accordance with claim 1, wherein the oxygen is added in step (b) as pure oxygen-enriched air and the oxygen-containing stream formed step (g) is at least partially recycle to the reactor in step (b).

6. A process in accordance with claim 5, wherein the portion of the oxygen and nitrogen containing stream produced in step (g) not recycled is vented to prevent accumulation of nitrogen in the system.

7. A process in accordance with claim 1, wherein each of said pairs of beds in said pressure swing adsorption unit is contained in a single vessel as discrete layers.

8. A process in accordance with claim 1, wherein at least a portion of the hydrogen-enriched stream is passed through the selective oxidation unit with the alkane and alkene-containing stream and recycled to the dehydrogenator.

9. A process in accordance with claim 1, wherein the effluent from the catalytic dehydrogenerator is passed through a second pressure swing adsorption unit to remove hydrogen therefrom prior to being introduced into the reactor in step (b).

10. A process in accordance with claim 9, wherein the hydrogen stream from the second pressure swing adsorption unit is recycled to the dehydrogenerator.

11. A process in accordance with claim 1, wherein the catalytic dehydrogenator is comprised of a series of at least three discrete catalytic reactors, the product stream containing said alkene and unreacted alkane is withdrawn from a reactor intermediate the first and last of said reactors, the gaseous flow between said reactors, including the reactor from which the product stream is withdrawn is passed through a heating means to raise the temperature thereof, the catalyst in the dehydrogenator is passed through all of said reactors regenerated and recycled to the first reactor, the recycle stream containing alkene, and unreacted alkane is passed directly from the pressure swing adsorption unit to the reactors in the dehydrogenator which follow in sequence the reactor from which the product stream was withdrawn thereby removing substantially all of the oxygen in said stream, and the effluent from said last reactor is introduced into the first reactor, a reactor other than the first reactor wherein the concentration of the alkene is approximately the same as that of said effluent or said reactor in step (b).

12. A process in accordance with claim 11, wherein the dehydogenerator contains at least four reactors and the product stream is withdrawn from the penultimate reactor.

13. A process in accordance with claim 11, wherein the effluent from said last reactor is introduced into the feed to said first reactor.

14. A process in accordance with claim 11, wherein the effluent from said last reactor is introduced into a reactor other than said first reactor wherein the concentration of the alkene is approximately the same as that of said effluent.

15. The process in accordance with claim 11, wherein the effluent from said last reactor is introduced into said reactor in step (b).

16. A process in accordance with claim 11, wherein the product stream withdrawn from the dehydrogenerator is passed through a second pressure swing adsorption unit to remove hydrogen therefrom prior to introduction into said reactor in step (b).

17. A process in accordance with claim 16, wherein the hydrogen-containing stream produced in the second pressure swing adsorption unit is recycled to the dehydrogenerator.

18. A process in accordance with claim 11, wherein the temperature in the dehydrogenerator is from about 500° to 800° C.

* * * * *